United States Patent
Fedrigon et al.

(10) Patent No.: US 6,336,891 B1
(45) Date of Patent: Jan. 8, 2002

(54) INTERACTIVE EXERCISE PAD SYSTEM

(75) Inventors: Richard Fedrigon, Oak Park, IL (US); Bruce R. Bacon, Forest Grove, OR (US); Michael F. Hilferty, Florence, MT (US); Scott R. Francis, Hollister; Loren M. Luke, San Mateo, both of CA (US)

(73) Assignee: Real Vision Corporation, Florence, MT (US)

( * ) Notice: Subject to any disclaimer, the term of this patent is extended or adjusted under 35 U.S.C. 154(b) by 0 days.

(21) Appl. No.: 09/308,719

(22) PCT Filed: Jan. 8, 1997

(86) PCT No.: PCT/US97/22024

§ 371 Date: May 21, 1999

§ 102(e) Date: May 21, 1999

(51) Int. Cl.[7] .............................. A63B 24/00
(52) U.S. Cl. .............. 482/8; 482/4; 482/902; 434/247
(58) Field of Search .......... 482/1–9, 900–902, 482/71, 72, 52, 54, 55, 57; 434/247; 345/802; 273/148 B

(56) References Cited

U.S. PATENT DOCUMENTS

| 4,925,189 A | | 5/1990 | Braeuning |
| 5,049,079 A | | 9/1991 | Furtado et al. |
| 5,076,584 A | | 12/1991 | Openiano |
| 5,334,997 A | * | 8/1994 | Scallon ..................... 345/167 |
| 5,405,152 A | * | 4/1995 | Katanics et al. ............. 463/2 |
| 5,562,572 A | * | 10/1996 | Carmein ..................... 482/4 |

* cited by examiner

Primary Examiner—Glenn E. Richman
(74) Attorney, Agent, or Firm—Dorsey & Whitney LLP

(57) ABSTRACT

An interactive exercise pad system (10) receives exercise data (108) from a user (24) stepping on and off of an exercise pad (12). The exercise data (108) is optionally pre-processed in a data acquisition unit 14, before being communicated to a communications port (30) of a computer (16). The computer (16) obtains data files (82) which have been pre-stored on media (80). The data files (82) include video files (84), optional audio files (86), and table files (88) of location and terrain information. The video files (84) and the table files (88) are collected from a real exercise course. The computer (16) processes the exercise data (108) and the data files (82) to playback the video files (84) and the optional audio files (86) so that the user (24) experiences a realistic simulation of the real exercise course.

32 Claims, 6 Drawing Sheets

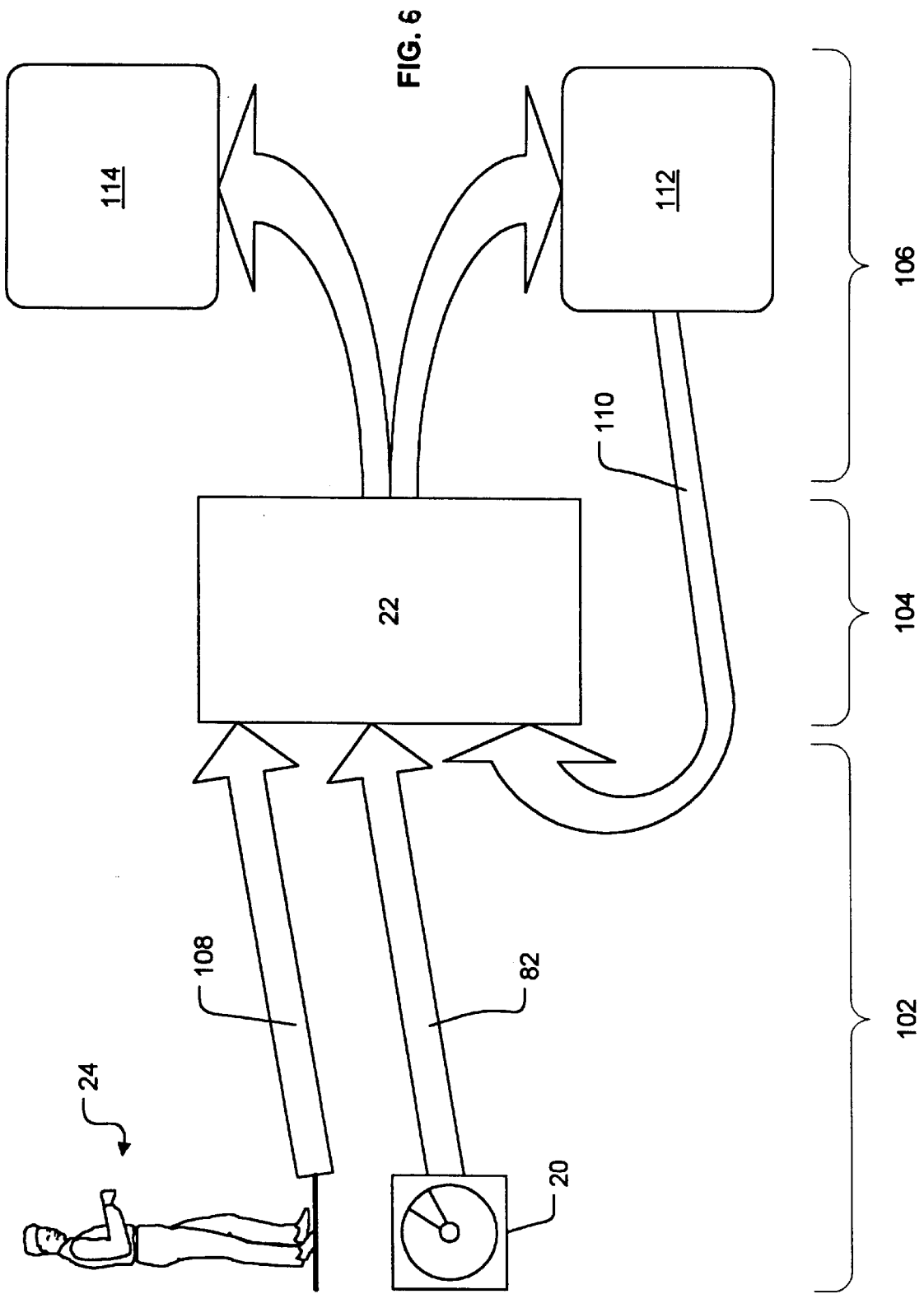

INTERACTIVE EXERCISE PAD SYSTEM

TECHNICAL FIELD

The present invention relates generally to exercise equipment, and more particularly to an interactive exercise pad system which simulates real world exercise courses to users as they perform walking, running, jumping, and dancing exercise regimes.

BACKGROUND ART

Exercise is necessary. Medical studies have related important health problems to the lack of it, and it clearly affects our moods, our sense of self-image, and the public image by which others perceive us. However, increasingly people are not getting the amounts or the types of exercise which they need. Many reasons exist for this, but some particular ones are boredom, self consciousness, the difficulty or inability to go somewhere to exercise, and even complex social pressures.

Exercise is considered boring, and repetitive exercise is considered particularly so. A major reason for this is that exercise today frequently is not practical in natural or varied settings. For example, to walk or run in many urban settings there may be little choice but to use an inside location at a health club or gym, and to use that same facility day after day. When people do want to exercise, finding a suitable place to do so can therefore be difficult. A health club, gym, or park may not be conveniently near by, or may be too crowded with others also seeking exercise or even unrelated use of the facility.

Somewhat related to the where-to-exercise issue are time issues. Travel to public indoor exercise facilities takes time, and upon arrival there may be a wait to use the exercise resource of preference. There is also the matter of being able to exercise when one wants. Health clubs and gyms may keep set hours limiting when certain equipment is generally available, or they may even be closed during some hours of the day. Similarly, crime in some places has reached the deplorable state that nighttime use of parks is dangerous, and increasingly even outright prohibited. And as our society increasingly turns to flexible schedules and working at home (particularly as new telecommuting capabilities so permit), these time constraints upon when one can exercise become even more apparent and burdensome.

Exercising in traditionally public settings such as health clubs and gyms can also be awkward feeling or even embarrassing to many. Some people are simply shy, and do not want to exercise where they are constantly reminded that they are surrounded by other people, or by people whom they do not know. Others are self conscious about their own physical condition, particularly in a "comparative" setting like a health club, and they are therefore uncomfortable (unfortunately such people may need exercise the most, for instance because they are overweight).

In sum, there are many complicated reasons why we do not exercise, and some of these may never be entirely overcome. However, furthering exercise to the extent possible is a worthy goal. Today many see perception of the exercise environment as a key to increasing the participation in, the enjoyment of, and ultimately the success of exercise. Thus efforts are being made to change the exercise environment, with some of the rationale being if one cannot exercise in a natural manner (e.g., in a park), then use equipment to work the same muscles in the same manner; if one cannot go to a natural setting, then create the illusion of one; and if one cannot go somewhere to exercise (e.g., a health club or gym), then bring exercise to the user (e.g., to the home, office, or hotel room).

The current situation, and the focus on the exercise environment, have created large and growing specialty segments in the exercise equipment market. And the home and office segment is one example. But regrettably it is one which has to date not been very successful at delivering what its consumers want. Those who do exercise with the equipment available in this market segment find that they do not enjoy and can not stick with exercise for very long because the home and office settings are often full of distractions and exercise there is boring. "Virtual Reality" exercise equipment is another such market segment (one which has potential overlap with the home and office market segment, but one which has largely failed to do so to date). Several major exercise equipment manufacturers (e.g., TECTRIX NAUTILUS, LIFE FITNESS, TRANSCAPE, KETTLER, PRECOR, AND REEBOK) have developed exercise machines having such capability, but these overwhelmingly rely upon animated computer graphics and are expensive. It is generally perceived in the industry that the development costs of animated computer environments are prohibitive, therefore consumer price resistance is anticipated by manufacturers and their product offerings are accordingly fewer in this segment.

The present invention acknowledges that exercise environment is the key. However, the term "virtual reality" is not entirely appropriate, and the approach disclosed herein may more appropriately be termed "natural environment simulation."

DISCLOSURE OF INVENTION

Accordingly, it is an object of the present invention to provide an exercise system which dynamically simulates exercise in a natural environment.

Another object of the invention is to provide an exercise system which realistically simulates exercise in a natural environment.

And, another object of the invention is to provide an exercise system which is economical and which uses equipment and methods that are conventional enough that relatively unsophisticated users may employ the system for exercise in public facilities as well as private settings.

Briefly, one preferred embodiment of the present invention is an interactive exercise system which includes an exercise pad and a detector for detecting when a user steps on and off of the pad. The detector produces event data which is communicated to a computer. Also provided to the computer are data files from storage media which include course and image data captured from a real world exercise course. The computer processes this various data and directs presentation of the image data on a display in a manner such that the user experiences a realistic simulation of both exercising in and traveling through the exercise course. Further, although optional, a data acquisition unit may be added to receive the event data and pre-process it by debouncing, filtering, or converting it into another format before it is communicated onward to the computer.

An advantage of the present invention is that very dynamic exercise may be carried out with it, yet without undue user involvement in setting effort levels for the exercise. A user may, optionally, initially set a nominal difficulty level, and then let the inventive exercise system dynamically control the pace thereafter.

Another advantage of the invention is that it realistically simulates a real world exercise experience. Real-world or true nature video content is used, which is captured in natural settings along real world courses, rather than computer animation and graphics, or such superimposed upon nature still scenes. Optionally natural sound content may be added, or the user may opt for verbal feedback and encouragement, or for music to set a particular mood or to entertain.

Another advantage of the invention is that it is economical to implement and operate. It may employ relatively conventional computer equipment using relatively standard audio and video hardware, and using widely used and well understood operating system software. The media used by the invention to store audio, video, terrain information, and optional other files may be any of many widely available and inexpensive formats, and accordingly media units containing exercise sessions can be quickly and relatively cheaply produced, reproduced, and distributed to the ultimate users of the invention.

Another advantage of the invention is that it allows a user to conveniently exercise in the privacy to a home, an office, or a hotel room. The invention may employ an exercise pad which is very compact and storable (and therefore easily transportable) and a laptop (or even palmtop) computer having a display and a media player such as CD or DVD player. But since many people have and travel with such computer hardware already, very little additional needs to be purchased, packed or set-up to take advantage of the invention.

Another advantage of the invention is that it has a very high entertainment value, drawing and engaging its users in a realistic and natural exercise environment, which promotes regular exercise and adherence to exercise regimes, and which decreases the seductive ability of distractions to interrupt exercise sessions.

And, another advantage of the invention is that it appeals to a very broad range of potential users. Children will find the experience of their movement causing scenic video interaction to be very stimulating, and they may also design their own competitions and games, such as determining who is faster using the exercise pad and data display. Busy adults can employ the invention in the home, for example, in the kitchen while preparing meals or in the den while watching television. They can also grab brief exercise breaks, say while diverting attention back and forth between the scenic video interaction of the invention and important television broadcast news items. Similarly, the invention can be used in the office or the shop, either as a temporary respite from traditional work tasks or even in conjunction with such. For example, a computer user may even employ the invention while sitting at their workstation, with the feedback from the invention occupying only a small additional window on their display. Business people away from home on trips can now easily maintain their regular exercise regimes in their hotel rooms by using the invention. And senior citizens can use the invention to supplement their regular walking programs, or use it indoors with options like a heart rate monitor, to insure safe use even if they are elderly or frail.

These and other objects and advantages of the present invention will become clear to those skilled in the art in view of the description of the best presently known mode of carrying out the invention and the industrial applicability of the preferred embodiment as described herein and as illustrated in the several figures of the drawings.

BRIEF DESCRIPTION OF THE DRAWINGS

The purposes and advantages of the present invention will be apparent from the following detailed description in conjunction with the appended drawings in which:

FIG. 6 is a block diagram depicting the major inputs, processes, and outputs in the invention, and the flow of data through the invention.

BEST MODE FOR CARRYING OUT THE INVENTION

Figure 1:
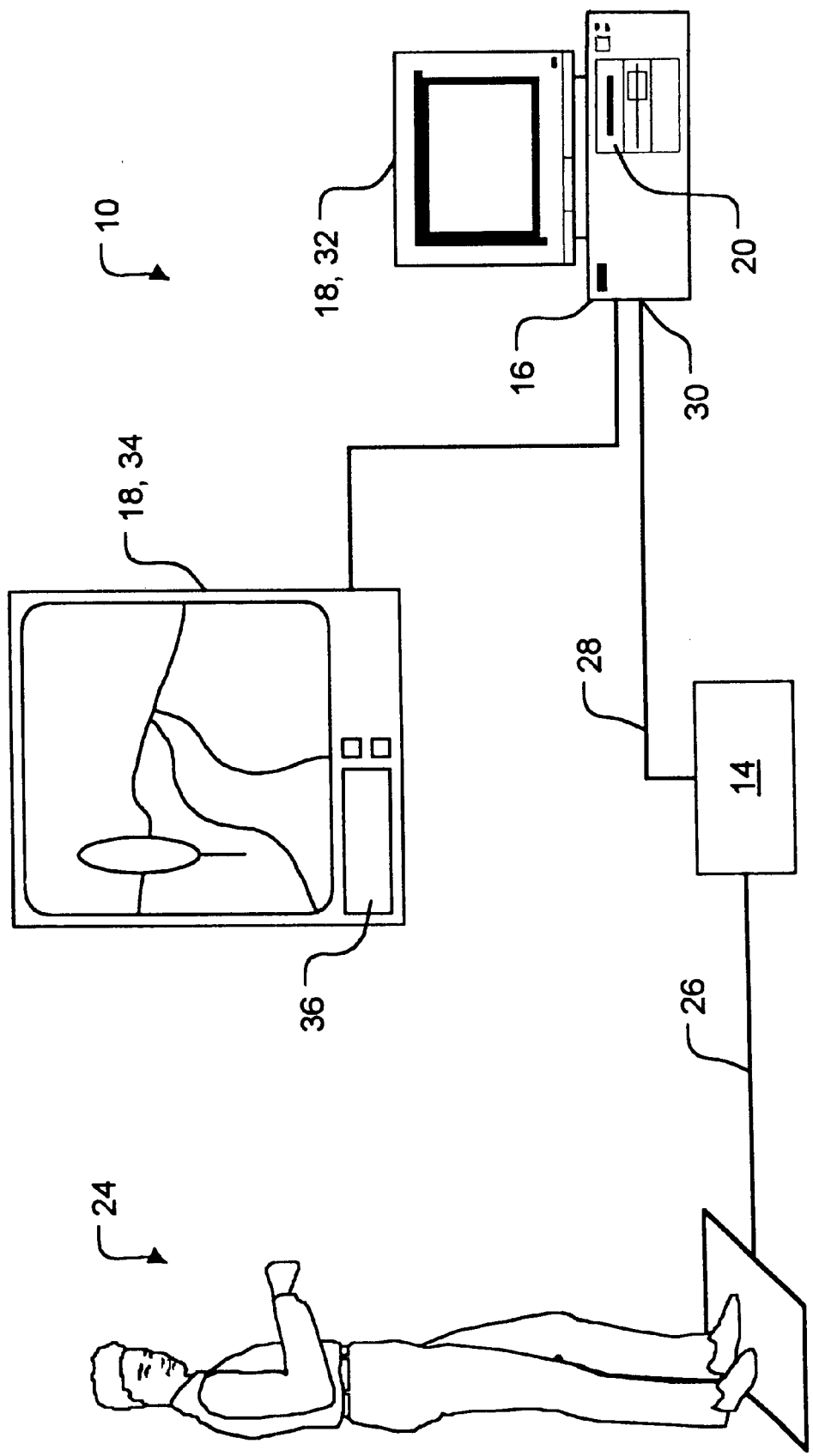
FIG. 1 a depiction of a user applying the present invention in a typical usage scenario, emphasizing the major components of the preferred embodiment.

A preferred embodiment of the present invention is an interactive exercise pad system. As illustrated in the various drawings herein, and particularly in the view of FIG. 1, a form of this embodiment of the inventive device is depicted by the general reference character 10.

FIG. 1 illustrates the major component parts of the preferred embodiment of the exercise pad system (EPS 10). Included are an exercise pad 12, a data acquisition unit (DAU 14), a computer 16, a display 18, a media player 20, and software 22 (FIG. 6) which runs on the computer 16 and permits control of and beneficial use of the EPS 10 by a user 24. A first cable 26 connects the exercise pad 12 to the DAU 14, and a second cable 28 connects the DAU 14 to a communications port 30 on the computer 16. In FIG. 1 the display 18 being shown is actually two physical units, a computer monitor 32 and a television 34 which includes a speaker 36.

Figure 2:
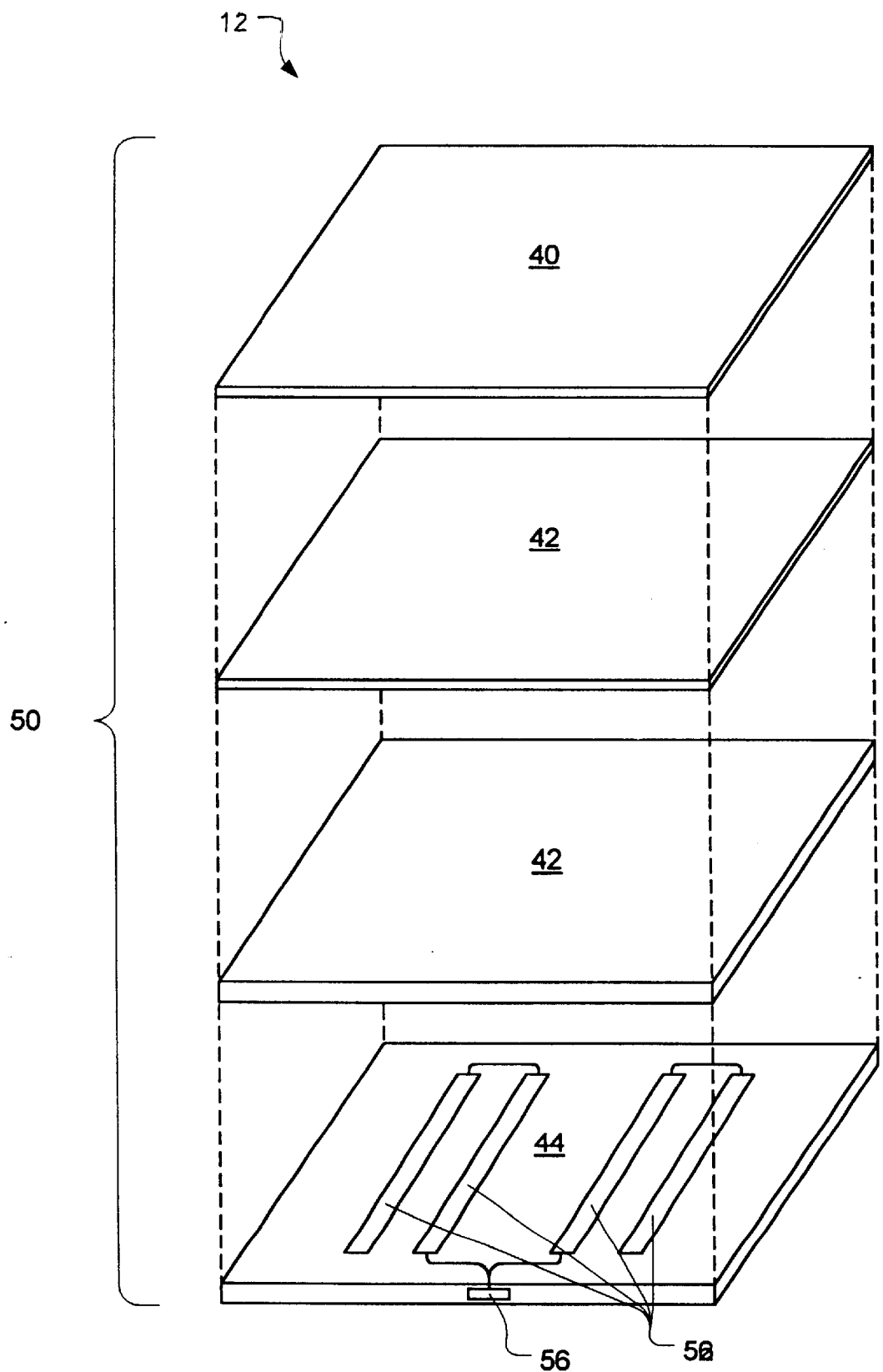
FIG. 2 depicts in exploded view exercise pad component being used in FIG. 1.

FIG. 2 illustrates the exercise pad 12 of FIG. 1. Included are a mat 50, a set of switches 52 having contacts 54 included (not shown, but number for reference), and a connector 56 which permits attachment of the first cable 26 so that an electrical signal from the DAU 14 is brought to and can be switched by the contacts 54 of the switches 52.

The mat 50 is made of suitably durable materials which can withstand a heavy user 24 striking it repeatedly by jumping up and down, say one million times in one concentrated area, without substantial material breakdown or wear occurring. The currently preferred mat 50 is up of a number of layers. As can be seen in FIG. 2, a top layer 40, intermediate layers 42, and a bottom layer 44 are provided. The top layer 40 provides wear resistance and presents a slightly textured surface to the user 24. The uppermost of the intermediate layers 42 provides overall stiffening, which results in better force distribution, both for transfer to the switches 52 below, and to cushion the impact as perceived by the user 24. The lowermost intermediate layer 42 is of a springy or spongy material (e.g. an open-celled neoprene material), to work in concert with the other intermediate layer 42. Finally, the bottom layer 44, supports the switches 52, and provides a suitable floor contacting surface for the mat 50. Many types of inexpensive and widely available materials are suitable, including rubberized materials or even Styrofoam (™) materials. The inventors prefer a closed-cell vinyl sponge matting material in ⅜" thickness. Cardiovascular matting is readily available, with various surface textures available. The size of the mat 50 (and thus also the exercise pad 12) may be small, say 20" by 24"(0.5 by 0.75 m) for running in place, or much larger, say 48" by 48"(1.5 by 1.5 m) for dancing.

The switches 52 are such that the weight of the user 24 causes the contacts 54 to close when the exercise pad 12 is stood upon, and to reopen quickly once that weight is removed. Various types and shapes of switches 52, and methods for incorporating them into the exercise pad 12, can be used. For example, long, narrow, flexible types of switches 52 are available which can be bonded under the mat 50 using adhesive. Pressure track type switches 52 are also available that allow for easy replacement if they wear out. Flexible array grids of small membrane type switches 52 wired in parallel over the sensitized area of the exercise pad 12 may also be used for portable embodiments of the EPS 10 which are rollable or foldable. And the digitally acting switch 52 so far described could even be replaced with an analog sensing unit (entirely eliminating the contacts 54), with considerable addition of complexity in other components like the DAU 14 and the software 22, but which might be useful for some sophisticated embodiments of the EPS 10.

As noted, the preferred embodiment uses normally open type contacts 54 in the switches 52, although normally closed variations may also be used. This is preferred because simple parallel connection works well with such, and depending upon the other electrical circuitry used, normally closed types may result in current flow for long periods when no user 24 is actually using the exercise pad 12. One concern is prompt contact 54 reopening after a user 24 steps off of the exercise pad 12. For this, a 60 ms response time is considered by the inventors to be more than sufficient, since 16 steps per second is an anticipated maximum. Further, the presence of inherent weight from the mat 50 which is over the switches 52 makes some nominal spring strength (springiness) separating the contacts 54 important.

Another concern is debouncing of the electrical signal created by the opening and closing of the contacts 54. In the preferred embodiment, signal processing is performed in the DAU 14 to remove bounce effects. Suitable component choice for the switch 52 itself this can reduce or even effectively eliminate the need for signal processing, but is hard to achieve for a range of users 24 and types of exercise. Finally, the connector 56 is provided on the exercise pad 12 at a suitable and convenient point for connection of the first cable 26. It is connected electrically to the contacts 54 of the switch 52.

Of course, alternate embodiments of the exercise pad 12 are easily possible, using one or more switches 52 in various electrical configurations (e.g., in parallel, in serial, or in combinations thereof), with appropriate increases in the number of the contacts 54 and conductors in the connector 56 as needed. Or, the switches 52 may be replaced with a pressure sensor, and the DAU 14, the computer 16, and the software 22 suitably enhanced to retrieve and process the more detailed user 24 impact data which such an embodiment could produce.

Some pads (structurally similar to the exercise pad 12) are already commercially available, coming constructed with an embedded switch 52 assembly having contacts 54 separated by a insulating springy or spongy material. The footstep of a user 24 compresses this material and causes ridges in the contacts 54 to make contact with the conductive material (i.e., opposed contacts 54) on the other side of the spongy material. Alternately, mats 50 can be purchased with indentations already in the bottom for mounting switches 52.

Unfortunately, these existing pads are most commonly used for security and safety matting around dangerous equipment, and to count foot traffic. Security type pads, in particular, are often over engineered. Often they are designed to handle even fork lift trucks running over them. Expensive switch redundancy is sometimes also included due to stringent safety requirements. And the signal outputs of these may be unsuitable, being merely intended to warn of some presence upon the pad, rather than to communicate precisely when that presence began and ended. Also, these pads are primarily sensors, and only minimally impact absorbers, rarely being cushioned to the satisfaction of a prospective exercise user 24. Alternately, some available pads are not durable enough for this particular type of exercise application, being instead constructed to receive the distributed wear of users 24 walking across or stepping randomly upon their entire exposed surface, rather than to receive very localized and very repetitive impacts which may be considerably heavier than mere footsteps (say from a dance step or from the user 24 jumping in place). Accordingly, in view of its particular use in the EPS 10, the inventors find it more appealing to manufacture the exercise pad 12.

Figure 3:
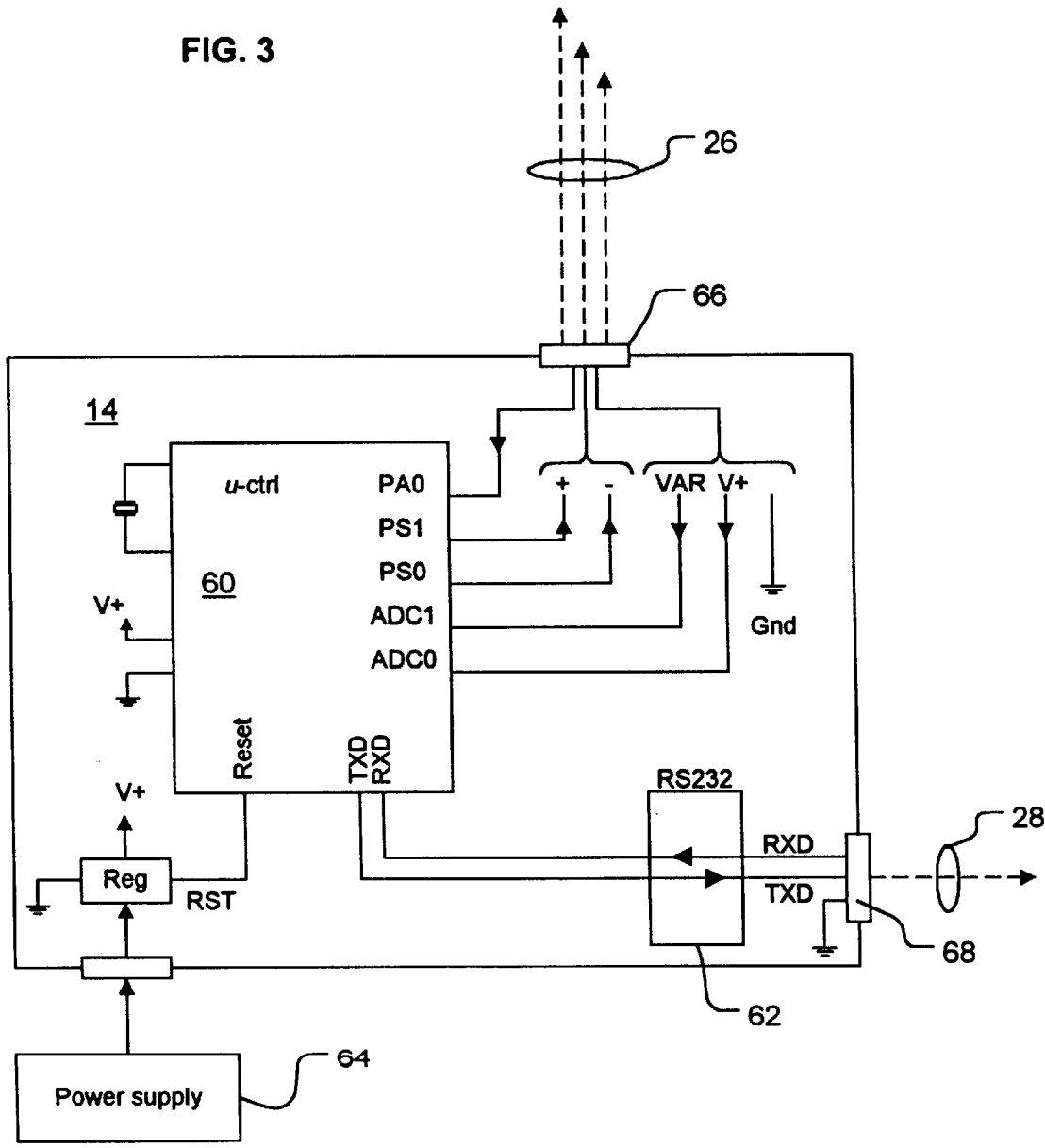
FIG. 3 is a stylized block diagram of the data acquisition component of the invention.

FIG. 3 illustrates a preferred version of the DAU 14. Included are a micro controller 60; a communications driver 62; a power supply 64; a first port 66, for connection to the first cable 26; and a second port 68, for connection to the second cable 28. The DAU 14 provides power for the switch 52 via the first port 66, and receives back an electrical signal containing exercise data 108 about the opening and closing of the contacts 54. The micro controller 60 suitably processes the exercise data 108 (e.g., debouncing it, filtering it, etc.) and directs the communications driver 62 so that the exercise data 108 containing information about the state of the switch 52 is communicated via the second port 68 to the computer 16.

In the preferred embodiment the DAU 14 measures the time interval between each successive step and sends this information as the exercise data 108 to the software 22, which is running on the computer 16. When the exercise data 108 is received, one of two algorithms may then be used by the software 22 to advance the video frame rate of real world video as it is played back on the display 18 to the exercising user 24. The software 22 can use the actual measured time interval value between each successive step event to advance the frame rate. Alternatively, the software 22 can ignore the actual reported time interval value, but count the occurrence of a valid interval value as indication that a step event has occurred. The number of step events averaged over a small time period is then used to determine the new frame rate. In either case an averaging algorithm (e.g., a generic averaging algorithm such as currently used in heart rate monitors) is desirable to ensure that the played back video frame rate is smooth. For example, take the last x number of speed or interval measurements and average them. Then use this average value for speed display and to advance the video. Relying on the average of the last x measurements results in this manner results in more stability then responding to one measurement alone) The software 22 is discussed further below.

The power supply 64 is optional, and in the currently preferred embodiment it is omitted. Instead the second cable 28 is used to parasitically obtain power directly from the communications port 30 of the computer 16 for the DAU 14, and thus via the first cable 26 also for the exercise pad 12. However, wireless varieties of such communications ports 30 are becoming increasingly common, and to use them some form of power supply 64 becomes necessary. When present, the power supply 64 can include a transformer and rectifier system, a battery, or even a power generating unit in the exercise pad 12 (for example a piezoelectric unit which converts a portion of the impact energy from the user 24 into electricity).

The DAU 14 can be made quite small, and in theory even entirely integrated into the exercise pad 12. However, this increases the possibility of damage from user 24 impact. The DAU 14 can also be placed directly at the communications port 30 of the computer 16. However, this carries the unfortunate connotation of a dongle, which many computer users dislike. Both of these alternates for the location of the DAU 14 permit elimination of either the first cable 26 or the second cable 28, respectively. Alternately, using small enough components, such as increasingly common surface mount devices, the DAU 14 may be entirely integrated into a cable. The preferred location for the DAU 14 is as shown in FIG. 1, and it is protected with a small hardened plastic case or other such durable packaging, to make it suitable for use in robust exercise environments.

It should also be noted that the DAU 14 itself is actually also optional. By replacing the first cable 26, the DAU 14, and the second cable 28 with just a suitable cable, and by connecting the exercise pad 12 to the communications port 30 of the computer 16, and by using suitable software 22 a simple embodiment of the EPS 10 is possible. Via such a single cable, the power for the switch 52 can be obtained directly form the communications port 30 and the software 22 can monitor one or more inputs of the communications port 30 for simple state changes of the switches 52. In theory, for such embodiments even rudimentary signal processing like debouncing, if needed, can be handled by the software 22. However as noted, such embodiments are simple, having limited capability. And as also previously noted, being difficult to engineer to work reliably for wide ranges of exercise types and user 24 weights.

The computer 16 (FIG. 1) may be any suitable system, and the inventors anticipate that most embodiments of the invention will use personal computers (PC's; although even mainframe types are theoretically useable). Laptop type computers are particularly suitable, because the exercise pad 12 can be made quite small and easily compatible for storage, for example by rolling it up. Thus users 24 traveling away from the home or the office can easily maintain their regular exercise regimes by using such an exercise pad 12 and a laptop computer 16. Further, since many potential users 24 already own or use suitable computers 16, the other components of the EPS 10 are all that would need to be purchased, thus potentially making the EPS 10 a very economical exercise system.

As shown in FIG. 1, the EPS 10 can employ a computer monitor 32 to present the user 24 with feedback from the software 22 (say with a GUI and statistical feedback), and to playback previously recorded media from the media player 20 on a television 34. Many computers 16 today have video hardware which includes a PC to TV (television) port. This allows for the use a normal television 34 up to 150 feet away, typically via a coaxial cable. Such a television 34 type hook-ups would allow users 24 to exercise away from the actual location of the computer 16. (Of course, a suitable extension cable would also be required to connect the DAU 14 in such an embodiment.) It should also be kept in mind that only one display 18 is actually needed.

The speaker 36 is also optional, but will probably be provided in most embodiments, since all televisions 34 and most computers 16 today have sound capability.

The media player 20 may be a CD-ROM or DVD player, or other player for still other possible media types. The media player 20 may even be eliminated as a local component, with the content of previously recorded media being brought to the computer 16 over a network (say as a video stream over the Internet). Thus network computer (NC) versions of the computer 16 are also suitable.

Figure 4:
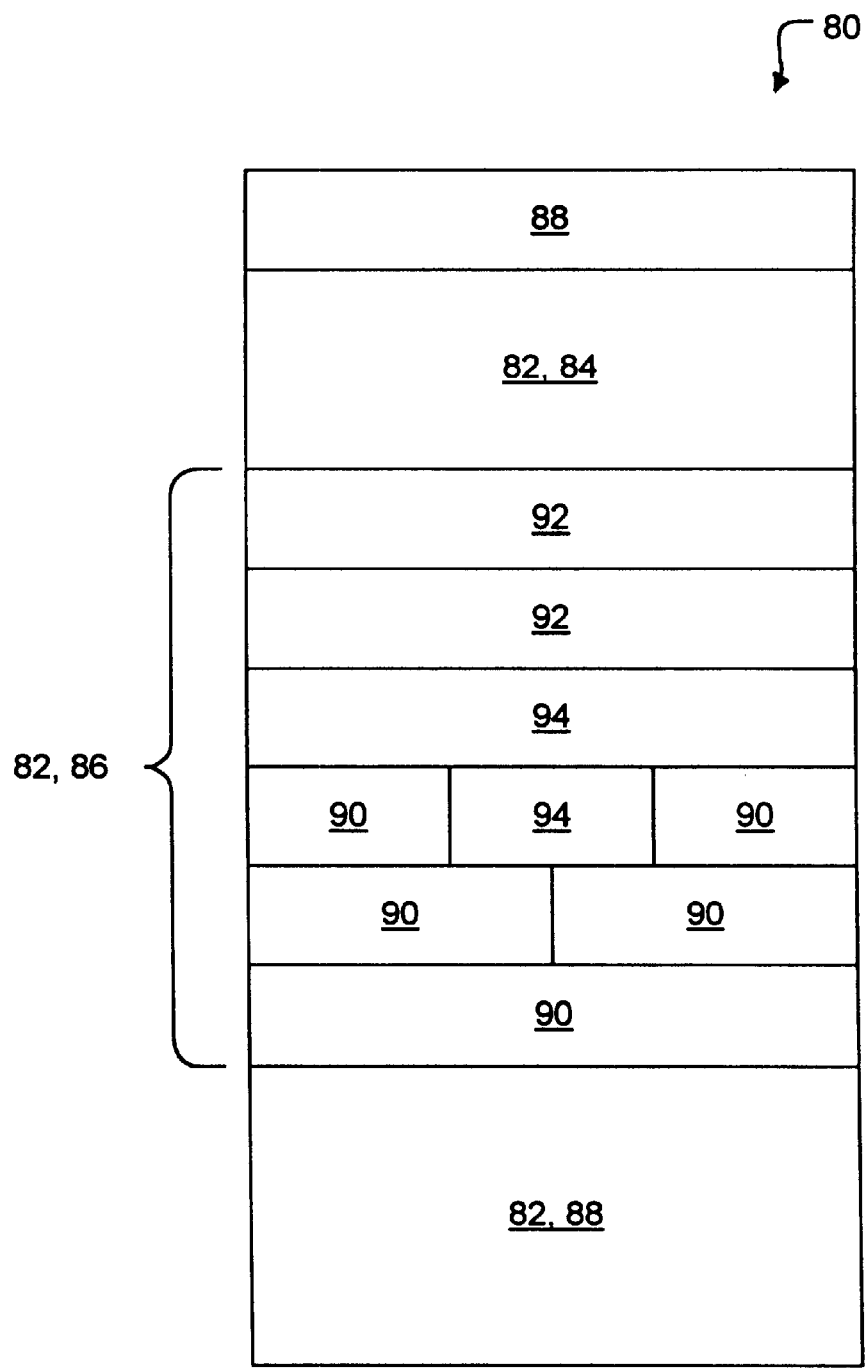
FIG. 4 is a block diagram which is representational of files stored on pre-recorded media which the invention may use.

FIG. 4 illustrates a preferred version of media 80 which is suitable for playback in the media player 20, or for network transmission to the computer 16 (thus note that the media 80 therefore does not necessarily have to have a tangible physical presence at the site of the rest of the EPS 10). Included are three general types of pre-recorded data files 82: video files 84 (e.g., compressed AVI or MOV formats; typically one per unit of media 80, but not necessarily so), audio files 86 (e.g., in WAV or MIDI formats), and table files 88 of normalized terrain characteristic data which associate terrain characteristics to particular times in the video file 84.

The video files 84, in particular, are different from those used in known prior art systems. The EPS 10 does not use mere computer animations or graphics as the primary genre to present a visual substitute for a real-world exercise courses (techniques which are notoriously labor intensive and therefore time consuming and expensive). Instead the EPS 10 uses actual captured image sequences of such real-world courses (i.e., "real-world" video). This fundamental distinction makes exercise with the EPS 10 much more lifelike, and additionally makes it much cheaper to develop the media 80. Of course, computer animations or graphics can still be used with the EPS 10, say as sprites for pacers or for avatars of users 24, which are overlaid onto the playback of the real-world video files 84 as the user 24 exercises. However, such use is entirely optional and will probably be limited in amount even in embodiments where it is used Multiple types of audio files 86 may be provided. Two of these, voice audio files 90 and music audio files 92 are used in generally conventional manners (e.g., to instruct, motivate, set tempo, and to entertain). However, another type of audio file 86 may also be used by the invention which is not typical: environmental audio files 94 (e.g., of animal sounds such as bird calls, wind in the trees, and running water). The use of environmental sounds to enhance simulations of nature has long been known, but not to the inventors' knowledge in the context of exercise systems. As noted, prior art systems have relied primarily upon computer animations, and the sound content of these, where even provided, has generally had similarly cartoon-like qualities.

Of course, the EPS 10 can use sound in other manners (conventional and otherwise), if desired. For one example, sounds such as cheering for good performance can be used (conventional). Notably, this type of sound can be either played back directly from prerecorded recorded audio files 86, or retrieved from an audio file 86 and then tailored appropriately (say by tying intensity to pace for some specified time duration), or the sound may be generated in the computer 16 based upon criteria stored in an audio file 86. Another example is the sound of barking dogs as a motivation that the user 24 exceed a certain pace to get rid of the "chasing" dogs (a somewhat unconventional instance). In sum, there are lots of ways to use sound to motivate and control the exercise experience, and the inventive EPS 10 is quite capable of employing these.

The media 80 used with the EPS 10 are produced by acquiring position and terrain characteristics of real-world courses for the table files 88, by acquiring video data for the video files 84 which is representative of a human viewer's perspective as they would travel through the exercise course, and by acquiring audio data for the audio files 86 (e.g., by dubbing in voice overs and music soundtracks or natural environment sounds to match the acquired terrain and video data), and by storing all of these along with synchronizing information in the media 80. This generalized approach of mapping normalized terrain characteristic data into the table files 88 facilitates the creation of new video environments. The terrain characteristic data is simultaneously collected with the video data using a time interval which ensures that changes in terrain characteristic seems smooth and continuous to the user 24.

The terrain characteristic types used by the EPS 10 can be quite varied. When the inventors initially developed the EPS 10, they appreciated that many real world courses had variations in running surface, say from earthen path to sandy beach to asphalt running track. Further, terrain characteristics which may not easily be simulated directly (e.g., altitude or temperature variation, or even slope may nonetheless be recorded in the data files 82, and the software 22 used to control the EPS 10 in a suitable manner to apply a variable "handicap"(or more preferably termed, an "indirect feedback") which simulates the varying effort levels required of users 24 on such a real world course. For example, the EPS 10 may vary the speed of the video in accordance with slope. In the preferred embodiment the video is advanced as a function of user 24 foot speed only, as a product of some constant, k. Generally it is a flat grade for the running environment is assumed, so k never changes. However slope data may be used to change this constant k. Thus, when a user 24 is running up a steep slope, the video frame rate can be reduced for a given foot speed by making k smaller for this particular hill simulation. Similarly, running downhill, the constant, k, can be made slightly larger. And using a pacer feature would emphasize this even more.

Indirect feedback can also be used to anticipate particular exercise scenarios, based upon exercise session characteristics up to a present point or even based on statistically gathered information about users 24. An example of possible indirect feedback is a grade interaction algorithm where video frame rate a function of both step rate and grade. Also terrain information (e.g., slope or grade data) can be used to create the illusion of increased effort to climb a positive grade being presented in the video playback. For example, as the user 24 comes to a steep climb in the video, the software 22 reads the slope data associated with this climb then decreases the step/distance constant (or stride hang time/distance constant) that is used to advance the video. Consequently, if the user 24 maintains the same step rate on an increasing grade section, the video frame rate slows down for that unchanged pace by the user 24. For the user 24 to maintain their pace, reflecting their progress in the video environment, an increased exercise intensity is used to compensate for the hill grade, until the user 24 crests the hill. Similarly, the step/distance constant can be increased slightly by the software 22 for downhill segments. (Note: the variation of the constant for the downhill case will not be as great as the variation for the uphill case for a running model.) This algorithm results in the EPS 10 functionally simulating hill climbing effects without the use of complex machinery such as pitch controls on treadmills. As background, some simple exercise equipment today measures exercise intensity by reading gear RPM (exercycles, Nordic Tracks, treadmills, etc.) or by measuring exercise repetitions. This measured value is multiplied by some appropriate constant to register a speed value that the user monitors. In the EPS 10 his constant may be varied as a function of the reported grade (terrain) information associated with the video data, which adds another level of realism to the simulation.

For implementations of the software 22 using such indirect feedback, fuzzy logic techniques may be beneficially employed. Accordingly, there is quite broad variety of terrain characteristics which are appropriate for recording in the media 80, and the true spirit of the present inventive EPS 10 encompasses that variety.

Figure 5:
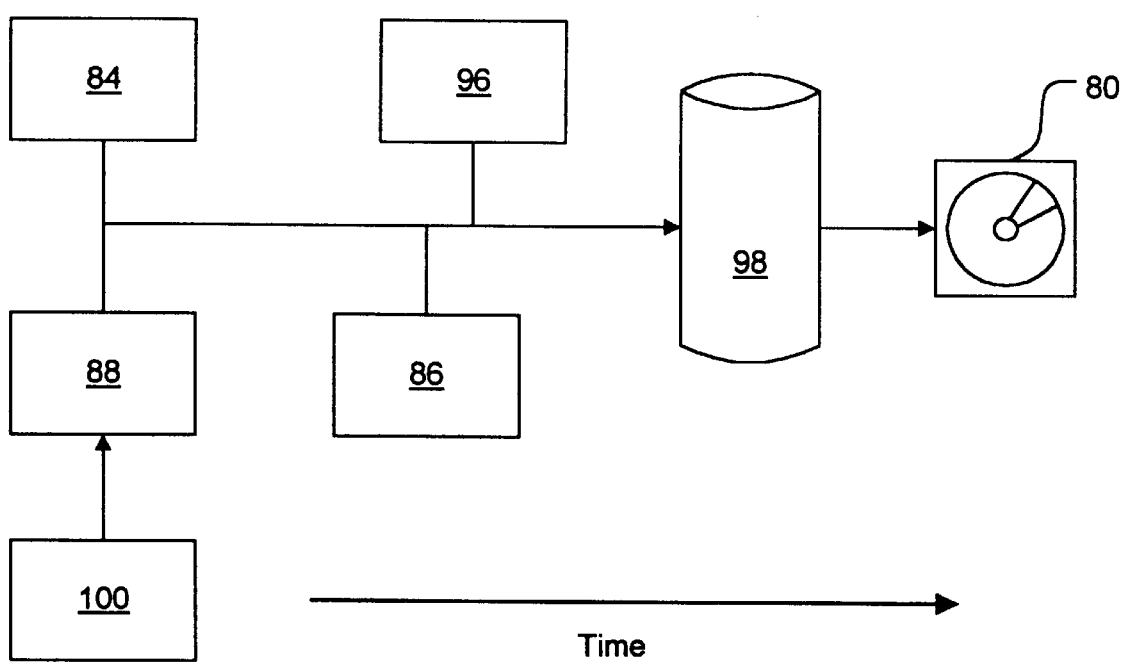
FIG. 5 is a block diagram depicting sources and a timeline for collection of data used to record the media.

To enhance the quality of the terrain data and its correlation to data in the video files 84, it may be obtained by reference to accurate standards 100 (FIG. 5). The inventors' preferred embodiment uses reference to a Global Positioning Satellite system (GPS). However, it should be appreciated that ground based radio frequency, optical, and other long used conventional systems can all be used for such standards 100. Similarly, pedometers, altimeters, odometers, inclinometers, and even manual addition of terrain information based upon visual previews of courses are other examples of suitable standards 100 which may be employed.

Also of particular advantage for the EPS 10 is that the software 22 may selectively employ the contents of the table files 88. The inventors have previously worked on development of interactive exercise systems utilizing exercise equipment like exercycles, treadmills, steppers, etc., and in creating suitable media for such systems additional various terrain characteristics are desirable, such as slope and various equipment characteristics like bicycle gears. The inventive EPS 10 can use media 80 which have such detail in the table files 88, by simply ignoring the irrelevant content, or by using it for the indirect feedback purposes discussed above.

The media 80 may also contain a software program 96, for loading into and execution on the computer 16 as the software 22. However, this is not a requirement. The software 22 may be supplied separately (e.g., downloaded from a bulletin board, BBS, or an Internet site), and the software 22 which is executed will typically be stored in mass storage on the computer 16, rather than present as a software program 96 and loaded from on the media 80 before each use. Thus all of the capacity of units of the media 80 may be dedicated to use for the data files 82. Alternately, a version of the software program 96 may be included in some (not necessarily all) instances of the media 80, and if an existing version of the software 22 detects that the software program 96 stored on the media 80 is newer (i.e., an upgrade, entirely or in part), the user 24 may be prompted whether they want to install the new version from the media 80 into the computer 16 for use thereafter. Further, still additional types of data may also be stored on the media 80 (e.g., video driver updates for the computer 16). This is particularly important because there are actually two types of software which are critical for obtaining optimum benefit from the EPS 10. There is the video engine, which must be installed on the computer 16 as effectively part of the BIOS and the operating system (OS), and there is the software 22 of the EPS 10 itself. On most computers 16 today the video engine is quite distinctly part of either or both of the BIOS and the OS levels only (which are often both upgradeable today), while the EPS 10 appropriately belongs at only the applications level. Continuing patches and enhancements of video engines may be released by either the video hardware manufacturer or by the OS provider, but distribution of these is spotty. Since the EPS 10 benefits by using the best video engine available, the newest releases of the most widely used video engines can simply be included on the media 80.

FIG. 5 shows the major elements of the data files 82 in a timeline format as they are recorded in the media 80. The data for the video files 84 and data for the table files 88 are collected simultaneously into a temporary database 98. The audio files 86 and optionally the software program 96 are then added to complete the database 98 and the media 80 is written. The audio files 86 and the software program 96 may be added to the database 98 at any time relative to collecting the data for the video files 84. This is the case even for environmental audio files 94, which may be captured in a real world setting (but not necessarily the same one as that for the video files 84), or which may be derived from "stock" data for natural sounds, or which may not even have their origins in true nature settings.

FIG. 6 depicts how the software 22 directs inputs 102, processes 104, and outputs 106. The inputs 102 are the user 24 generated exercise data 108 from the DAU 14, the data files 82 from the media 80, and also user data 110 which the user 24 themselves provide at a graphical user interface (GUI 112). The processes 104 include statistical manipulation of the exercise data 108 and correlation of a "virtual" position of the user 24 to an effective position within the exercise course described in the data files 82. The outputs 106 are the GUI 112 and playback 114. The GUI 112 communicates with the user 24, and the playback 114 entertains the user 24. The inputs 102 have largely been covered already, and the processes 104 are more easily understood in view of the desired outputs 106, so the outputs 106 are discussed first.

The GUI 112 informs the user 24 about the state of the EPS 10 and displays feedback based upon statistical manipulations of the exercise data 108. However, since productive statistical analysis requires some basis of comparison, default "average person" values are be pre-stored in the software 22 (or stored and input from the media 80), and used for weight and metabolic factors when determining the calories consumed by the user 24. Alternately, the GUI 112 may solicit from the user 24 personal information such as weight and age, and preference information such as exercise goals and difficulty, and use this to override the defaults. In the preferred embodiment, an "average person" stride length is similarly used as user 24 overrideable default in determining equivalent distance traveled and speed values.

After obtaining the user data 110, both the exercise data 108 and the user data 110 are processed to provide feedback to the user 24 while he or she exercises. Examples include elapsed time, total steps, current step rate, average step rate, equivalent running distance, equivalent running speed, total calories burned, etc. during an exercise session. More sophisticated capabilities can easily be added as options in the GUI 112. For example, a simple pacer window may be added, to graphically show the relative position of the user 24 (say as one sprite) to a predefined pace rate (a second sprite). This allows the user 24 to visually reference his or her running rate to a predefined pace. Such a pacer window may also depict position in both graphical and numerical formats. Or networked instances of the computers 16 can be used by multiple users 24 for competitions, with avatars used to represent the individual users 24. Of course, in keeping with what have become conventional aspects of most graphical user interfaces today, the elements of the GUI 112 can be opened, closed, resized, minimized, and maximized as desired by the user 24.

As has somewhat already been covered, the EPS 10 may use both a separate computer monitor 32 for displaying the GUI 112 and a separate television 34 for displaying the visual portions of the playback 114. Or the EPS 10 may simply use one display 18 (most likely a computer monitor 32, but not necessarily so) and display different items in different windows.

The playback 114 includes selective presentation of the video files 84 and the audio files 86 from the media 80, based upon the table files 88, the exercise data 108, and the user data 110. To increase or decrease the apparent rate of presentation of the video files 84 the rate can be adjusted (analogous to frame rate for motion picture film or scan rate for television), or portions (i.e., frames and even groups of frames) may be dropped to simulate the speed which the user 24 is "virtually" traveling with respect to the particular exercise course.

Unfortunately, sounds are not so easily manipulated. Unlike image sequences with rates above 30 frames per second, which are perceived to some degree as simply "moving" despite how much the rate varies, the human ear is good at "averaging" sound data without the listener detecting quality degradation. To handle this sets of different audio files 86 many be stored on the media 80 (e.g., different music selections simply for variety or appropriateness with different paces of exercise, or different levels and types of verbal feedback and coaching, or even different gender or language voice content, which may be requested by the user 24 in the user data 110). Selective playing back of such audio files 86, based upon their appropriateness in the particular situation, are therefore sufficient for most embodiments of the EPS 10.

In the preferred embodiment, the software 22 employs a time based model to compute speed and position within a simulated exercise course at roughly 60 ms intervals (or 100 ms, the interval is relatively unimportant). The DAU 14 feeds data to the software 22 asynchronously, and the data files 82 roughly corresponding to the current "position" in the exercise course are then fetched and processed and the appropriate playback rates are synchronized. In particular, the video file 84 position is synchronized with the virtual position of the user 24 within the simulated exercise course, but even some of the audio files 86 may also be synchronized (e.g., speech characteristics for voice audio files 90 and pitch for environmental audio files 94 can be changed). This time based model is interrupted by the arrival of new data, and runs an extra cycle to re-compute speed and position when it arrives. Therefore, in the preferred embodiment the DAU 14 transmits such data at a rate of up to once every 60 ms, with more frequent transmissions improving the smoothness of the computations. However, the synchronization rate used for video file 84 playback is somewhat complicated by the fact that the video timing is variable and need not necessarily correlate with real time.

For the actual playback of the video files 84, conventional ActiveMovie filtergraphs are used in the preferred embodiment to produce the desired output characteristics. This provides considerable flexibility, permitting the use of different "movie" formats and permitting the software 22 to include extensive user 24 command capabilities, like play, pause, resume, reset, and stop. Further, in the preferred embodiment, the software 22 is used to influence EPS 10 playback speed with a function using a denominator of 1,000 to convert the integer value speed data received into a floating point value to provide adjustment resolution and permit the user to have a considerable degree of control so that they may fine tune their exercise experience.

Many aspects of the software 22 may be conventional. For example, widely used techniques for the for playback of video and audio data exist, including ones for varying the speed of such playback (e.g., the already noted ActiveMovie technology). Similarly known are techniques for storing data tables and controlling micro processor and communications circuitry. Thus, while creation of the software 22 is a major task, it is nonetheless one will within the capability of skilled programmers using present computer languages. The inventors presently use Visual C++ and the Microsoft Foundation Class library (both ™ of Microsoft) to write the 32 bit routines for communicating with the micro controller 60 used in the DAU 14, and they use ActiveMovie to play back video files 84 in AVI or MOV file formats. This also permits the software 22 to run well under the widely used WINDOWS95 and WINDOWSNT operating systems (both ™ of Microsoft Corp. of Redmond, Wash.), which currently are and which can be anticipated to continue to be widely used in computers 16 for some time.

In operation, the EPS 10 is highly user interactive. However, the interactive features are not intrusive, as is the case for many prior art systems. A setup procedure in the software 22 provides instruction on the set-up of the exercise pad 12, and accepts any user data 110 provided. The user 24 is also asked to specify a desired nominal level of difficulty at which they would like to exercise (e.g., easy, realistic, hard; which then permits feedback to the user 24 which may be quite simple or even as complex as a graphical pacer) the type and parameters of audio output desired (e.g., volume, music or nature sounds, etc.), and what feedback information they would like to additionally see while exercising (e.g., pulse, speed, distance, calories, etc.). This information as feedback can be displayed on the display 18 (e.g., superimposed upon the video playback). Thus, a user 24 may setup the EPS 10 once for a particular exercise pad 12 and exercise sessions (storing the preferences in a personal profile file), and then changing this information only as needed. The user 24 does not have to bother with anything further thereafter, because the EPS 10 can take over. Of course, value added features such as terrain characteristic graphs and the relative course location of the user 24 can also easily be provided, in pop-up or floating windows on the display 18. Once this is complete, the EPS 10 initializes itself to accept exercise data 108 which is captured by the DAU 14.

The inventors currently have two main algorithms which are considered appropriate for use in the software 22. The first of these uses the actual measured time interval between user 24 steps which is reported by the DAU 14 to the computer 16, to determine and control the apparent velocity in the displayed content presented on the display 18. This time interval information is then also used to control the current video frame rate. However, one issue here is the possible resulting jerky video movement caused by the responsive measurement of quick variations in the step rate of the user 24. To compensate for this an averaging algorithm is added to ensure a stable frame rate as the video file 84 is displayed as part of the playback 114.

The second algorithm uses the presence of a time interval value in a transmission packet as an indication that a step event has occurred at the exercise pad 12. The actual time interval value can be ignored. Such step events are then counted and averaged over a small time interval (say the last two to four seconds) to determine a step rate, and this calculated step rate is then used to determine a new frame rate as the video file 84 is displayed as part of the playback 114. The benefit of this algorithm is that it inherently helps to stabilizes the frame rate to correct for erratic step movements on the exercise pad 12.

Actually both algorithms require an additional averaging algorithm to stabilize the frame rate. The first algorithm has the step rate information implicit in the interval data sent from the DAU 14. This step rate information is then updated on every transmission. The second algorithm relies on the computer 16 to determine the step rate based on frequency of step event transmissions from the DAU 14. The step rate is then calculated by the computer 16, based upon the frequency of these events. In either case, the video rate would otherwise be choppy unless an averaging algorithm is added.

For use, the exercise pad 12 is conveniently placed within comfortable viewing distance of the display 18 and the user 24 acts-in-place (e.g., runs roughly in place) anywhere on the exercise pad 12. As the user 24 moves the frame rate of the video file 84 is advanced proportionally to the measured step rate and the playback 114 is presented.

The user 24 may also set goals. Currently, an indoor exerciser normally sets a goal of running for some time duration or for some distance, represented by a reported number from the exercise machine. However, in the natural environment simulation presented by the EPS 10, the user can choose the goal of running to the red farmhouse, canyon road, or waterfall in a given video which may be 3 miles from the start of the video sequence. This creates a much more meaningful and enjoyable goal as opposed to the unimaginative idea of just running on treadmill for 3 miles or 20 minutes. The inventors term this Visual Goal Motivational Benefit.

Of course the EPS 10 is not limited to just running-in-place. Special interactive scenic videos with music and coaching can use dance steps on the exercise pad 12, and again the value of their uplifting dancing exercise.

Similar to the dance example, children may find jumping rope on the running pad to be entertaining and informative with respect to their jump speed. Also, jumping rope has become increasingly popular for adults due to the effectiveness of boxing workouts for rhythm, coordination, endurance, and speed. The running pad will had another dimension of motivational benefits for this activity.

After spending hours in front of a computer 16 which is being used for other purposes, a user 24 could get up for a few minutes and interact with a video session on the exercise pad 12 to become refreshed before returning to the other work on the computer 16. The exercise pad 12 could be placed under the feet of a user 24 while they are sitting on a chair in front of the computer monitor 32. The user 24 can keep the video window minimized or hidden while working on the computer 16, and their hyperactive foot activity may be recorded and later checked against the video to see how far the user has traveled, purely as a diversion.

The inventors also anticipate that using the EPS 10 as an aerobic hang time trainer for jumping exercises will become a major application. The measurement of hang time or time spent airborne is an ideal way to measure the intensity of such aerobic activity. This form of exercise on the EPS 10 is more analogous to a Stairclimber-type of exercise rather than a treadmill type. In the treadmill or running-in-place case, horizontal travel represented by step rate is measured. In the Stairclimber or jumping case, vertical travel represented by hang time is measured. To support this application the DAU 14 and the software 22 would need to be tailored for hang time measurements. The intensity of the jumping exercises is a function of the number of jumps taken, and the height of each individual jump. Therefore the DAU 14 would need to be capable of doing time interval measurements of pulse width instead of period. Remember that the contacts 54 of the switch 52 are open when the user 24 is leaping in the air and closed when he or she is on the exercise pad 12. Here what needs to be measured is the time that the contacts 54 are open only, but suitable embodiments of the DAU 14 for this are easily constructed. Then appropriate measurements can be made with only minor modifications to the already described software 22. The following procedure describes the process:

The user 24 activates or resets the software 22 (e.g. from a keyboard or mouse at the computer 16) and then steps onto the exercise pad 12. When the user 24 jumps, a time interval value is reported to the computer 16 by the DAU 14. This value is added to a variable reflecting total time airborne since the start of the present exercise routine. While the user 24 is on the exercise pad 12, no further valid time intervals will be reported by the DAU 14. On the next jump by the user 24, a new time interval is added to a "total time airborne" variable. The rate at which this "total time airborne" variable increases is then used to advance the rate of the playback 114. An averaging algorithm is used to ensure smooth display of the video files 84. Since the jumping action reflects a climbing metaphor, feedback reflecting vertical distance traveled is appropriate. A possible video subject for this type of exercise might be a Pikes Peak hill climb course or some steadily climbing mountain path. A graph should also be added to the GUI 112. This graph could record total time airborne (or equivalent vertical distance traveled) versus total elapsed exercise time.

Hang time data is a good indicator of individual user 24 performance, since the results are not a function of assumed step length, as in a running-in-place model. Further, just measuring the number of steps taken by a user 24 is not necessarily sufficient for proper comparison, because the sensitivity of the switch in the exercise pad 12 is also somewhat a contributing variable. For example, light, short, choppy steps could not be well distinguished from full weighted vigorous steps. Consequently, since hang time values are a fairly accurate reflection of exercise performance, record performances could be listed for various men and women age categories for 6 minute, 12 minute and other time intervals, say on an Internet website.

An anaerobic hang time application could also be implemented using the EPS 10. This would use the exercise pad 12, the DAU 14, and a suitable version of the software 22. It would also require a small second PAUSE/READY switch. This switch could easily be wired to an input line on the DAU 14. The function of the switch would stop the DAU 14 from sending interval data to the computer 16, thereby allowing the user 24 to disable measurement when he or she wants to step off the exercise pad 12. The state of the switch could be easily displayed on the display 18 as well.

The EPS 10 here would be initially in a pause mode. The user 24 would then step onto the exercise pad 12 and press the PAUSE/READY switch to activate hang time measurement. When the user 24 jumps, the time interval of the jump would be reported to the computer 16 by the DAU 14. The software 22 could then generate a bar reflecting the time (or equivalent vertical leap) on a bar graph as part of the GUI 112. Each leap could then generate another bar, and if the user 24 wants to get off the exercise pad 12 and prepare for a next effort, he or she simply presses the PAUSE/READY switch and steps off the exercise pad 12 to "psyche-up." Then, when ready to try again, the user 24 steps back onto the exercise pad 12, presses the PAUSE/READY switch again, and makes a new jump. This application would particularly appeal to football, basketball, speed athletes, and anyone wanting to do plyometric type exercise. Coaches would also find it to be an important exercise tool to develop leaping ability for such athletes.

In addition to the above mentioned examples, various other modifications and alterations of the inventive EPS 10 may be made without departing from the invention. Accordingly, the above disclosure is not to be considered as limiting and the appended claims are to be interpreted as encompassing the true spirit and the entire scope of the invention.

INDUSTRIAL APPLICABILITY

The present EPS 10 is well suited for application in a wide variety of locations. Users 24 of the invention may easily employ the EPS 10 in the home and office as part of a dedicated exercise regime, or to exercise concurrently with other activities. For example, the users 24 may spend 10–30 minutes performing a complete aerobic workout with the EPS 10, they may take 3–5 minute commercial or work breaks to workout with the EPS 10, or they may perform other activities like watching television, preparing dinner, or working at their computer, all while concurrently using the EPS 10. The EPS 10 is also particularly well suited for use by traveling users 24 in their hotel rooms. Its non-computer components, like the exercise pad 12, can be constructed to be very light in weight and compactly storable, and the computer 16 itself may be a laptop type which the traveling user 24 is taking along for other reasons entirely. Further, although the inventors see the greatest potential of the invention as being for personal exercise, there is no reason why the EPS 10 can not also be used in conventional exercise settings like health clubs and gyms. And the inventors even envision commercial use for the EPS 10 in sporting goods stores and at sporting goods trade shows, as an adjunct in selling athletic shoes and possibly other goods. Currently such stores must let customers try out expensive merchandise like running shoes by letting them leave the premises or area, hoping that they are honest and will return, or else the customers must be restricted to running in nearby aisles or running in place on a mat, which the potential customers often find awkward and even embarrassing. By using the EPS 10 in such sales scenarios the customer (user 24) can try out the merchandise inside the store on an exercise pad 12, say with a large screen type display 18 so that they are engaged by the playback 114 rather than left feeling self conscious and the center of attraction in a high pressure sales environment.

The EPS 10 is also well suited for use by a very broad range of users 24, and even for a broad range of exercise types. Children naturally want to run and jump, and parents have long sought ways to get them to carry out such activities in one just place. The EPS 10 is at least a partial solution in this regard. It can be used to audio-visually engage and entertain younger children so that they do stay in one place, on the exercise pad 12 portion of the EPS 10. Somewhat older children can use the EPS 10 in conjunction with other physical activities, like solo rope jumping, or in competitive activities like running-in-place races or in jumping contests. Busy adults can use the EPS 10 for quick exercise breaks, say during television commercials or long computer file downloads, or for concurrent exercise at the kitchen countertop or at the shop table or at the computer workstation, or they may use the EPS 10 in a conventional manner for dedicated exercise sessions. For older adults such as seniors, and others who may want a slow to moderate exercise regime for recuperative purposes, the EPS 10 is particularly suitable. Unlike conventional heavy exercise equipment, like exercycles and treadmills, on which such users often over exert themselves, the EPS 10 naturally encourages reasoned and moderate workouts. One reason for this is because the EPS 10 itself is passive, in comparison to the noted conventional exercise equipment examples. However, another reason is that the EPS 10 can provide feedback to the user 24 which can make their exercise session safer and more controlled. Even in simpler embodiments the GUI 112 provides considerable feedback, and more sophisticated embodiments of the EPS 10 are easily possible, for example, ones which can accept specific user data 110 and even additional inputs from options like heart or breathing rate monitors, so that the user 24 can be cautioned and coached appropriately for their particular situation.

Multi-user applications using the EPS 10 are also quite possible. A version of the EPS 10 can have two or more exercise pads 12 connected to the DAU 14. Graphical sprites can then display the relative positions of the users 24, and a split screen on the display 18 can be implemented to show the relative positions if one user 24 lags too far behind. It is also anticipated that Internet or modem racing would be very possible with the EPS 10. By exchanging speed and distance data between the users 24 in real time, the users 24 could compete or pace with others in different locations via the integrated pacer feature. Data about the other progress of the other users 24 would be used to control the pacer displayed on the display 18. Such a pacer feature can be shown in a separate graphical window in the GUI 112, or it can be overlaid on the video presentation with the sprite of avatar of the user 24 superimposed progressively, say on a road being displayed.

The EPS 10 is also very suitable for segments of the exercise equipment market which have heretofore not been adequately served, including the entry level or low-priced equipment segment and particularly the interactive equipment segment (which effectively has no entry level or low-priced offerings presently). If the user 24 already has a computer 16, and if it can be setup for network (e.g., Internet) access to instances of the media 80, then use of the EPS 10 only requires purchase of the exercise pad 12, the DAU 14, and the cables (and as has been described herein, even the DAU 14 and the cables can be eliminated for some embodiments). Currently a rough majority of potential users 24 do have at least access to a suitable computer 16, but far fewer also have the appropriate network access. Accordingly, even in cases where network access is available, the inventors anticipate that most embodiments of the EPS 10 will include a local media player 20 which is suitable for reading media 80 which is in CD-ROM or DVD format. The user 24 can then play copies of the media 80 which are included as part of the purchased component package of the EPS 10, or they may obtain different media 80, say by purchase of cheap CD-ROM format units or by rental of DVD format units. In this manner the users 24 can easily and economically build their own or borrow from extensive libraries of interactive exercise sessions each having different real-world video content that is targeted toward different exercise goals and interests.

For the above, and other, reasons, it is expected that the EPS 10 of the present invention will have widespread industrial applicability. Therefore, it is expected that the commercial utility of the present invention will be extensive and long lasting.

What is claimed is:

1. An interactive exercise system, comprising:

a pad, suitable for being repeatedly stepped upon by a user;

detection means for detecting when said user steps on and off of said pad, and for creating event data based thereon;

a computer;

communications means for communicating said event data to said computer;

media containing previously stored data files which include course data and image data captured from a real exercise course;

media player means for playing back said data files to said computer;

display means for displaying said image data from said computer to said user; and said computer processes said event data and said course data, and directs presentation of said image data on said display means such that said user experiences a simulation of exercising in and traveling through said real exercise course.

2. The exercise system of claim 1, wherein said detection means includes at least one switch which is integrated into said pad and which has electrical contacts which are operated by the weight of said user stepping on and off of said pad.

3. The exercise system of claim 1, wherein said detection means includes a sensor which is integrated into said pad and which electrically generates said event data from said user stepping on and off of said pad.

4. The exercise system of claim 1, further comprising data acquisition means for acquiring said event data from said communications means in a raw format, for pre-processing said raw format into a pre-processed format, and for transmitting said pre-processed format of said event data to said computer with said communications means.

5. The exercise system of claim 4, wherein said pre-processed format is processed with at least one member of the set of operations consisting of debouncing, filtering, and amplifying.

6. The exercise system of claim 4, wherein said pre-processed format includes separate data for the event of said user stepping on and the event of said user stepping off of said exercise pad.

7. The exercise system of claim 4, wherein said pre-processed format includes data for the duration between said user stepping on and stepping off of said exercise pad.

8. The exercise system of claim 1, further comprising:

audio data which is further included in said data files;

audio means for playing said audio data from said computer to said user; and said computer additionally directs playing of said audio data on said audio means as part of said simulation of said real exercise course.

9. The exercise system of claim 8, wherein:

said audio data includes at least one member of the set consisting of verbal audio data, musical audio data, and environmental audio data; and said verbal audio data communicates encouragement and information to said user of the exercise system, said musical audio data amuses, entertains, and sets an appropriate mood while said user exercises with the exercise system, and said environmental audio data provides an illusion to users that exercise on the exercise system is occurring in said real exercise course.

10. The exercise system of claim 8, wherein said audio data is stored in at least one file storage format chosen from the set consisting of WAV and MIDI formats.

11. The exercise system of claim 1, wherein:

said image data further includes at least one member of the set consisting of textual data and graphical data; and said textual data communicates written information to said user of the exercise system, and said graphical image data communicates by informational graphically demonstration to said user of the exercise system.

12. The exercise system of claim 1, wherein said image data is stored in at least one file storage format chosen from the set consisting of AVI and MOV formats.

13. The exercise system of claim 1, wherein:
said display means includes video processing circuitry and a monitor included in said computer; and
said audio means includes sound processing circuitry and a speaker included in said computer.

14. The exercise system of claim 1, wherein:
said display means includes video processing circuitry included in said computer and a screen included in a television; and
said audio means includes sound processing circuitry included in said computer and a speaker included in said television.

15. The exercise system of claim 1, wherein said communications means includes at least one member of the set consisting of cables having electrical conductors, light beam transmission means, and radio frequency transmission means.

16. A method of controlling a simulation during exercise, comprising:
detecting event data based upon when a user steps on and off of a pad;
communicating said event data to a computer;
retrieving into said computer previously stored data files, said data files including course data and image data captured from a real exercise course;
processing said event data, said course data, and said image data in said computer; and
displaying said image data to said user based upon the results of said processing, such that said user experiences the simulation of exercising in and traveling through said real exercise course.

17. The method of claim 16, wherein said step of detecting includes detection of closure and opening of sets of contacts in at least one switch contained in said pad.

18. The method of claim 16, wherein said step of detecting includes sensing the presence and absence of weight upon said pad.

19. The method of claim 16, further comprising:
acquiring said event data in a raw format; and
pre-processing said even data from raw format into a pre-processed format, prior to said step of communicating said event data to said computer.

20. The method of claim 19, wherein said step of pre-processing includes at least one sub-step which is a member of the set consisting of debouncing, filtering, and amplifying said event data.

21. The method of claim 19, wherein said pre-processing includes differentiating between data for the event of said user stepping on and the event of said user stepping off of said pad.

22. The method of claim 19, wherein said pre-processing includes ascertaining the duration between said user stepping on and stepping off of said exercise pad.

23. The method of claim 16, further comprising playing audio data which is further included in said data files to said user as part of the simulation of said real exercise course.

24. The method of claim 23, wherein said step of playing audio data includes at least one sub-step which is a member of the set consisting of instructing, informing, entertaining, and encouraging said user.

25. The method of claim 24, wherein said step of playing video data includes at least one sub-step which is a member of the set consisting of instructing, informing, entertaining, and encouraging said user.

26. A method of making a storage media which is readable by a computer system to dynamically control a simulation of exercise in a real exercise course, the method comprising:
collecting location information for points along a real exercise course;
collecting terrain characteristic information for said points;
creating course data by associating said location information and said terrain characteristic information;
collecting video data including captured natural video image sequences; and
storing said course data and said video data in a computer readable media unit, thereby permitting the computer system reading an instance of said media unit to dynamically produce for users the simulation of traveling through said real exercise course.

27. The method of claim 26, further comprising storing audio data in said media unit, to instruct and amuse said users of the exercise machine as they exercise.

28. The method of claim 26, further comprising storing software for controlling the computer system in said media unit.

29. The method of claim 26, wherein said step of collecting location information includes referring to a position standard to determine positions of said points along said real exercise course, thereby permitting correlation of effective distances traveled by users of the exercise machine to geographic displacements of said points along said real exercise course.

30. The method of claim 29, wherein said position standard includes at least one member of the set comprising global position sensing systems, radio frequency triangulation systems, optical triangulation systems, altimeters, odometers, and inclinometers.

31. The method of claim 26, wherein said step of collecting force information includes measuring real forces present at said points along said real exercise course.

32. The method of claim 26, wherein said terrain characteristic information includes at least one member of the set comprising slope, altitude, temperature, wind speed, wind direction, current speed, current direction, and ground surface resilience.

* * * * *